(12) United States Patent
Herrick (10) Patent No.: US 6,290,684 B1
(45) Date of Patent: *Sep. 18, 2001

(54) PUNCTUM PLUG HAVING A COLLAPSIBLE EXPANDED SECTION AND DISTAL TIP EXTENDING SUBSTANTIALLY PERPENDICULAR THERETO AND METHOD OF INSERTING SAME

(75) Inventor: Robert S. Herrick, Rialto, CA (US)

(73) Assignee: Herrick Family Limited Partnership, Rancho, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/033,452

(22) Filed: Mar. 2, 1998

(51) Int. Cl.[7] .................................................. A61M 35/00
(52) U.S. Cl. ............................. 604/294; 128/887; 623/11
(58) Field of Search ........................... 604/8, 9, 10, 264, 604/265, 285, 289, 290, 294, 907, 523, 530, 540, 541; 606/198; 128/887, 898; 623/4, 11, 12, 66

(56) References Cited

U.S. PATENT DOCUMENTS

| | | | |
|---|---|---|---|
| 3,949,750 | * | 4/1976 | Freeman . |
| 4,461,295 | * | 7/1984 | Herrick . |
| 4,660,546 | * | 4/1987 | Herrick et al. ........................ 604/264 |
| 4,915,684 | * | 4/1990 | MacKeen et al. ........................ 604/8 |
| 4,959,048 | * | 9/1990 | Seder et al. .............................. 604/9 |
| 5,049,143 | * | 9/1991 | Gertner et al. ........................ 604/290 |
| 5,163,959 | * | 11/1992 | Herrick .................................... 623/11 |
| 5,171,270 | * | 12/1992 | Herrick .................................... 623/11 |
| 5,283,063 | * | 2/1994 | Freeman ................................. 604/294 |
| 5,318,513 | * | 6/1994 | Leib et al. ................................ 604/8 |
| 5,417,651 | * | 5/1995 | Guena et al. ............................. 604/8 |
| 5,723,005 | * | 3/1998 | Herrick .................................... 623/4 |
| 5,868,697 | * | 2/1999 | Richter et al. ........................... 604/8 |

* cited by examiner

Primary Examiner—John G. Weiss
Assistant Examiner—Jeremy Thissell
(74) Attorney, Agent, or Firm—Daniel J. Meaney, Jr.

(57) ABSTRACT

A punctum plug for insertion through a punctum opening of an eye and into the canaliculus to occlude the punctum opening and canaliculus is shown. The punctum plug, or implant, comprises an elongated member having a pair of spaced ends wherein one of the pair of ends includes a distal section, preferably in the form of collapsible expanded section which terminates in a distal tip which extends in a direction substantially normal or perpendicular to the central axis. The other end of the pair of ends includes a thin retaining lip which extends in an anterior direction and which is adapted to be oriented to extend beyond the edge of the punctum opening and to engage the lip margin defining the eyelid. The elongated member, including the collapsible expanded section and distal section, are formed of a dimension to pass through a punctum opening of an eye. A method for treating external eye condition due to a deficiency of tears utilizing the punctum plug is also shown.

44 Claims, 5 Drawing Sheets

PUNCTUM PLUG HAVING A COLLAPSIBLE EXPANDED SECTION AND DISTAL TIP EXTENDING SUBSTANTIALLY PERPENDICULAR THERETO AND METHOD OF INSERTING SAME

BACKGROUND OF THE INVENTION

1. Field of the Invention

This invention relates to a punctum plug adapted to be utilized in the treatment of a human eye having a deficiency of tears and more specifically relates to a punctum plug or implant having an elongated member including a central axis and having at one end thereof a distal section, which in the preferred embodiment is in the form of a collapsible expanded section, terminating in a distal tip which extends in a direction substantially normal or perpendicular to the central axis. At the other end thereof is a thin elongated retaining lip positioned to have the elongated tip extend in a generally anterior direction to extend over the punctum open and engage the lip margin of an eye upon insertion of the punctum plug or implant through a punctum opening. The elongated member including the distal section and collapsible expanded section are dimensioned to pass through the punctum opening of an eye.

This invention also relates to a method for treating external eye conditions due to a deficiency of tears utilizing the punctum plug or implant having at one end thereof a distal section, preferably in the form of a collapsible flared section, terminating in a distal tip which extends in a direction substantially normal to the central axis.

2. Description of the Prior Art

It is known in the art that certain eye problems are related to the volume of tears on the surface of the eyes. Certain of these problems include dry eyes, corneal ulcer, conjunctivitis, blepharitis, contact lens problems and many other external eye diseases.

One method for treating a deficiency of tears is disclosed in U.S. Pat. No. 4,660,546, and the invention thereof is wherein the inventor thereof is the same inventor of the present invention. U.S. Pat. No. 4,660,546 discloses a method for treating external human eye conditions due to a deficiency of tears which includes the step of temporarily blockading the canaliculus of the patient and observing over a preselected period of time the response of the patient's eye to the temporary blockage and to determine if any improvement in the eye condition has been achieved in response to the occlusion.

If an improvement in eye condition is noted, an implant is placed within the canaliculus of the eye of the patient. A temporary blockading of the canaliculus is performed by placing a dissolvable, removable element, which may be in the form of a collagen material or other dissolvable material such as, for example, catgut, in the canaliculus. Unless removed shortly after insertion, the dissolvable implant is absorbed by the body in approximately a two week period.

A determination is first made if the canaliculus blockage results in an improvement in the eye condition or other conditions caused by related nasal congestion warranting permanent blockage of the canaliculus, for example, the patient will respond to a partial 60% to 80% retention of constant tears.

If permanent blockage of the canaliculus is warranted, U.S. Pat. No. 4,660,546 discloses that the permanent blocking of the canaliculus is performed by utilizing a permanent implant. U.S. Pat. No. 4,660,546 discloses that the permanent implant is fabricated of a nonabsorbable or non-dissolvable material and is in the form of a cylindrically shaped central body having a tapered end or an end of reduced diameter to facilitate the implantation of the implant into and for removal of the implant from the canaliculus. Both the temporary collagen implant or other dissolvable material and the permanent implant disclosed in U.S. Pat. No. 4,660,546 are in the form of a cylindrically shaped central member having a predetermined diameter which may terminate at one end in a tapered end and which reduces in diameter as it slopes away from the central member to form a tapered tip to facilitate insertion of the implant through the punctum, and into the canaliculus. U.S. Pat. Nos. 4,660,546 and 5,049,146 discloses implants or lacrimal occluders which occlude the canaliculus.

U.S. Pat. No. 4,461,295, wherein the inventor thereof is the same as the inventor of the present invention, discloses another treatment method which is a method for laser punctal occlusion. It is known in the art that punctal occlusion has been proven to be an effective way of treating patients with conditions such as sinusitis, hay fever, middle eye infection (chronic), post nasal drip, front headache and other such conditions.

The treatment method disclosed by U.S. Pat. No. 4,461, 295 includes the use of a temporary suture to stitch the tear drainage canals of the eyes closed to determine if a greater tear volume on the surface of the eyes would improve certain eye problems. This diagnostic procedure has become known in the art as the Herrick Stitch Test. The Herrick Stitch Test is performed by anesthetizing the local area around the lower or upper punctum of the eye. A stitch is carefully placed to occlude the punctum by an eye surgeon utilizing magnification of the eye.

After a preselected period of time using the Herrick Stitch Test, the eye surgeon determines if the eye condition has improved, if so, then the eye surgeon permanently closes the punctum by using an ARGON laser. The punctum may be reopened at a later time if excess tearing is experienced. The reopening of the punctum can be performed by surgical and laser techniques, all as disclosed in U.S. Pat. No. 4,461,295.

It is also known in the art to utilize other plugs and or techniques for occluding the punctum. One plug device which is known in the art is referred to as a punctum plug which is described in an article by Jerre M. Freeman, MD, entitled "The Punctum Plug: Evaluation of a New Treatment for the Dry Eye" which appeared in the publication of the transcripts of the America Academy of Ophthalmology and Optometry, pages OP-874 through OP-879 (hereinafter referred to as the "Freeman Reference"). In addition, the same punctum plug is disclosed and described in U.S. Pat. No. 3,949,750.

The punctum plug disclosed in the Freeman Reference and in U.S. Pat. No. 3,949,750 is a plug which is adapted to be inserted into the upper and/or lower punctal openings of the eye to block or occlude the punctum. The punctum plug of Freeman is a rod-like plug formed with an oversized rigid or solid tip or barb portion that dilates and blockingly projects into the that portion of the canaliculus located adjacent the punctum opening.

The punctum plug has a smaller neck or waist portion around which the punctum sphincter ring or fibrous tissue defining the punctum opening tightens. The punctum plug has relatively large, smooth head portion which rests on top of the punctal opening and prevents the plug from passing down into the canaliculus. The smooth head portion is designed to be domed shaped to permit the head to rest in the lacrimal lake and against the conjunctiva and cornea with little irritation. The head portion functions to prevent the punctum plug from passing or migrating further into the canaliculus. The punctum plug of Freeman is subject to being inadvertently removed from the eye by the patient.

It is also known in the art to provide for a temporary closure of the punctum by heat using a light cautery around and in the punctal opening. The punctal closure procedure is disclosed in an article entitled "Diagnosis and Treatment of Keratoconjunctivitis Sicca" which appeared in a symposium on medical and surgical diseases of the cornea, transactions of the New Orleans Academy of Ophthalmology in 1980 at page 43 wherein the authors thereof were Jose I. Barraquer, MD and eight other authors (hereinafter referred to as the "Barraquer Reference").

The Barraquer Reference further discloses that other treatment methods of temporarily closing the punctum include use of gelatin plugs, cyanoacrylate adhesives and diathermy. The use of intracanalicular gelatin implants for treatment of eye conditions is described in an article entitled "INTRA-CANALICULER GELATIN IMPLANTS IN THE TREATMENT OF KERATO-CONJUNCTIVITIS SICCA" by Wallace S. Foulds which appeared in the Brit J. Ophthal (1961) in Volume 45 at pages 625 through 627, inclusive, (the "Foulds Reference"). The Foulds Reference discloses that occlusion of the lacrimal puncta can be performed by use of and insertion of a fine, water soluble gelatin rod into the punctal openings. The gelatin rod is formed from pure powdered gelatin to which a small quantity of distilled water has been added and is heated in a water bath until the gelatin dissolves and a thick gel results. By dipping a cold glass rod into the so prepared gelatin, and withdrawing the same, fine solid rods of gelatin were formed.

The so formed gelatin rods were then inserted into the canaliculus to provide a temporary blockage. As such, the gelatin rod implants, although very fragile, provide an alternate known means for temporarily blocking the canaliculus. If an improvement in eye condition is obtained, then permanent closure of the canaliculus may be warranted.

It is known in the art that a Schirmer's Tear Secretion Test can be utilized to measure gross tear secretion. If the results of the Schirmer Tear Secretion Test discloses that an insufficient portion of the tear secretion is retained on the eyes, a temporary or permanent occlusion of the canaliculus may prove helpful to improving the above described external eye conditions.

An improvement over the Freeman punctum plug, as described in U.S. Pat. No. 3,949,750, is shown in U.S. Pat. 4,915,684. U.S. Pat. No. 4,915,684 discloses a lacrimal fluid modulating device composed of a generally cylindrical body portion with an enlarged cap at one inlet and a tapered peripheral enlargement at an outlet end. The tapered peripheral enlargement is solid. An axial bore extends completely through the modulating device and is fashioned with an outlet end having an internal diameter which is preferably no less than 0.12 and no greater than 0.36 mm.

A tapered shaft punctum plug for occlusion of the punctum opening having a tapered shaft and including one end that terminates in a narrow neck and a concave dome and another end that terminates in a solid pointed nose is offered for sale by Eagle Vision under the trademark SUPER PLUG.

Another punctum plug that is commercially available for occluding the punctum opening is known as an UMBRELLA PLUG. The UMBRELLA PLUG has an elongated cylindrically shaped central member having one end that is cut at an angle relative to the central axis and terminates in a flat, circular washer like cap or collarette. The UMBRELLA PLUG has at its other end a collapsible umbrella shaped bulb which collapses like the closing of an umbrella during insertion of the umbrella shaped bulb through the punctum and when the umbrella has passed through the punctum opening, it then reverts back to an open position.

U.S. Pat. No. 5,417,651 discloses a punctum plug and probe for lacrimal pathology which includes a plug having a flange, a neck and a foot portion or bulb portion. The flange is inclined at an angle of approximately 130° with respect to the symmetry axis. The foot portion is radially flexible from its resting position towards the symmetry axis. The punctum plug constitutes a head for a metallic mandrel which functions as a probe. The probe follows the path of the lacrimal duct and can be deflected to draw it out of the nasal cavity. The structure of the punctum plug is similar to the UMBRELLA PLUG described above.

U.S. Pat. No. 5,318,513 discloses a fixation stent and a method for using the stent to repair canalicular lacerations and to block fluid flow through a canalicular canal. The stent, adapted to be inserted into a punctum of an eyelid, includes a flexible tube portion having a proximal end, a distal end, an inflatable portion in fluid contact communication with the distal end, and a plug for sealing and anchoring the proximal end with a body canal. The plug includes a T-top portion with a diameter greater than the diameter of he punctum that rests at two specific locations on the margin of the eyelid, thereby anchoring the proximal end of the stent at the margin of the eyelid.

As is evidenced by the above described prior art, the two approaches used to occlude the lacrimal drainage system are to: (a) occlude the punctum opening and that portion of the canaliculus adjacent the punctum opening, e.g., Freeman U.S. Pat. No. 3,949,750, U.S. Pat. No. 4,915,684 the SUPER PUNCTUM PLUG, the UMBRELLA PLUG and the head plug to support a mandrel as shown in U.S. Pat. No. 5,417,651; and (b) occlude the canaliculus at a location other than adjacent the punctum opening, e.g., U.S. Pat. Nos. 4,660,546 and 5,049,142. However, other implants which can be used to occlude the canaliculus both adjacent the punctum opening and at other locations in the canaliculus are U.S. Pat. Nos. 5,163,959 and 5,171,270 wherein the inventor thereof is the same inventor as in the present Application.

The use of a punctum plug as a head for a metallic mandrel which functions as a probe, e.g. U.S. Pat. No. 5,417,651 and for an anchor for a stent to repair canalicular lacerations and to block fluid flow through a canalicular canal, e.g. U.S. Pat. No. 5,318,513, basically are punctum plugs known in the art as described above.

U.S. Pat. No. 4,959,048 discloses a reversible, flexible, lacrimal duct occluder which is formed of a shaft having a low profile cap at one end and a rounded tip at the other end. The shaft has at least one, and preferably 1–3, conical ranges forward on the shaft between the ends. The rounded tip enters the punctum followed by the leading edge of the range(s) until the occluder bends at an acute angle relative to the axis of the shaft and enters the horizontal canalicular canal.

In practice, however, it has developed that the transition from that portion of the canaliculus adjacent the punctum opening, sometimes referred to as the vertical portion of this canaliculus, does not occur as a distinct transition point, but rather occurs through an intermediary section referred to as the ampula or sac which is anatomically an extension of that portion of the canaliculus that extends horizontally to the nasal sac.

Therefore, an implant which occludes the punctum opening and that portion of the canaliculus adjacent the punctum opening, depending on its length, can have a portion thereof located in the ampula or sac. By occluding the lacrimal drainage system in this manner, it is not necessary that the implant physically be located in that portion of the canaliculus which is beyond the ampula or sac to be effective.

On the other hand, if an implant, without a dome or collarette, is inserted into the punctum opening or the vertical section of the canaliculus, that implant generally migrates through the punctum opening through the portion of the canaliculus adjacent to the punctum opening, into the ampula or sac, and can easily migrate into that portion of the canaliculus beyond the ampula or sac.

SUMMARY OF THE PRESENT INVENTION

The present invention discloses a new, novel and unique punctum plug or implant comprising an elongated member having central axis and a pair of spaced ends. In this invention, one of said pair of ends includes a distal section, which in the preferred embodiment includes a collapsible expanded section, terminating in a distal tip which extends in a direction substantially normal or perpendicular to the central axis. The elongated member including the distal section and the collapsible expanded section are formed of a dimension to pass through a punctum opening of an eye.

In the preferred embodiment of the present invention, the punctum plug or implant is adapted to be inserted into the punctum opening of an eye and to be transported into that part of the canaliculus adjacent the punctum opening between the punctum opening and the ampula or sac. If the implant is of sufficient length the distal section can be transported into or through the ampula of the canaliculus to occlude the punctum opening and that portion of the canaliculus adjacent the punctum opening. The punctum plug includes an elongated member having a first end and a spaced, opposed second end and a central member. In the preferred embodiment, the first end is slightly angularly disposed from the second end. The second end has a collapsible flared section which terminates in an outer edge or ring having dimension which is greater than the cross-sectional dimension of the central member. The collapsible flared section has an expanded position and a collapsed position wherein the dimension of the collapsed position is approximately equal to the geometrical dimension of the punctum opening of an eye adapted to receive the same. The application of a radial force to the collapsible flared section in a direction to collapse the outer edge thereof urges the collapsible flared section from its extended position into its collapsed position. If the length of the punctum plug is selected to keep the collapsible flared section within the that portion of the canaliculus adjacent the punctum opening, the clamping force developed between the collapsible flared section and interior side walls of the canaliculus holds the punctum plug in place.

If the punctum plug has sufficient length, once the collapsible flared section passes through the punctum opening and that portion of the canaliculus adjacent the punctum opening and into the ampula or sac, the collapsible flared section reverts back to its substantially extended position. The canalicular implant may be fabricated from a biodegradable material if it is to be used as a temporary implant, or may be formed of a non-biodegradable material if it is to be used as a permanent implant.

The known prior art implants for providing temporary and permanent occlusion of the punctum opening has certain disadvantages. One disadvantage is that a temporary implant, disclosed by the prior art, may have to be removed before it has been fully dissolved or absorbed, as the case may be. If the eye surgeon is unable to remove any part of or all of the temporary implant, the portion of the temporary implant not removed must remain in the canaliculus until it ultimately is dissolved in the body thereby terminating the occlusion of the canaliculus.

Typically, an eye surgeon will utilize the temporary implant as a means for determining if the permanent occlusion of the canaliculi will result in an improvement of eye conditions as described hereinbefore. It is possible for the temporary collagen implant if inserted into the punctum opening or into that portion of the canaliculus adjacent to the punctum opening, for example, to migrate into that portion of the canaliculus located beyond the ampula or sac or back out of the eye or to otherwise not remain in place. Also, the temporary implants may be too fragile to remove in a single piece during removal thereof, if required, by the eye surgeon.

In addition, the insertion and use of a permanent implant having a central body and a tapered end, which is usually formed of a nonabsorbable or non-dissolvable material, can be utilized to permanently occlude either that portion of the canaliculus located between the punctum opening and ampula or sac. However, such a permanent implant can still migrate within the lacrimal system and into that portion of the canaliculus located beyond the ampula or sac or out of the eye. Any migration of a permanent implant is undesirable.

The laser treatment to obtain punctal occlusion, although quite effective, has certain disadvantages. One disadvantage is injection of a local anesthetic is required and the patient may experience some pain or discomfort for one to two days after the procedure. Also, some discharge may occur for seven to ten days. Vision may be blurred for a few days. If the patient wears contact lens, the contact lens may be uncomfortable for a few days.

The other known punctum plugs have a convex dome or collarette to act as a cap to prevent the punctum plug from migrating through the punctum opening, through that lateral portion of the canaliculus adjacent the punctum opening, into the ampula or sac or into the medial portion of the canaliculus beyond the ampula or sac. Such caps are generally circular and result in an edge which engages, contacts or otherwise abrades the cornea.

Therefore, one advantage of the canalicular implant of the present invention is that the punctum plug or implant, when passed in the punctum opening into the lateral portion of the canaliculus, will be held in place and restricted from movement by a thin elongated lip which is located on the elongated member to position the tip to extend in a generally anterior direction and which is urged against the edge or sphincter muscle of the punctum opening and the lid margin. The collapsible expanded section of the implant, which in the preferred embodiment is a collapsible flared section, is located within that portion of the canaliculus, or lateral portion of the canaliculus, or within the ampula or sac.

Another advantage of the present invention is that the implant includes a collapsible expanded section which has an outer edge which is slideably urged against the interior walls of the punctum opening during insertion and placement within that portion of the canaliculus adjacent the punctum opening to hold the implant in position while concurrently occluding the canaliculus.

Another advantage of the present invention is that the canalicular implant is relatively easy to insert without the necessity of using an injectable anesthetic.

Another advantage of the present invention is that the permanent implant, when positioned in the punctum opening and that portion of the canaliculus adjacent the punctum opening, does not cause any tissue irritation or irritation to the eye due to migration of the same out of the canaliculus and through the punctum opening into the eye.

Another advantage of the present invention is that the punctum plug or implant is easily removable and does not cause any discomfort. Further, the punctum plug or implant does not cause any pain to the patient or to the cornea of the eye of a patient, there is no discharge for several days. In addition, upon removal of a punctum plug or an implant utilizing the teachings of the present invention, the patient's vision is not subject to blurring for several days and, if the patient wears a contact lens, the contact lens will not be uncomfortable for several days.

Another advantage of the present invention is that due to the holding action between the collapsible expanded section of the medial end of the implant and the thin elongated lip which is located on the elongated member to position the tip to extend in a generally anterior direction and which is urged against the edge or sphincter muscle of the punctum opening and the lid margin, the canalicular implant cannot be easily or readily dislodged by patient activity or movement.

Another advantage of the present invention is that the punctum plug or implant causes no long term discomfort to the user when the same is in place.

Another advantage of the present invention is that the punctum plug or implant is effective in blocking a drainage of tears through the punctum opening and that portion of the canaliculus adjacent the punctum opening. Thus, if only a partial blockage of drainage of tears is required, the punctum plug or implant can having a fluid metering opening extending axially therethrough.

Another advantage of the present invention is the collapsible expanded section of the punctum plug or implant can include a hollowed out central area which defines a thin walled, conical-shaped flared section.

Another advantage of the present invention is that the thin walled, conical-shaped flared section can terminate in an outer edge.

Another advantage of the present invention is that the elongated member may have a slight angular curve to urge the thin retaining lip into engagement with the edge of the punctum opening and away from the cornea.

Another advantage of the present invention is that the collapsible flared section can be non-uniform such as being cut at a bias or having a non-circular cross-section, such as being elliptically shaped.

Another advantage of the present invention is that the collapsible flared section of the canalicular implant can include a tool receiving opening in the central section thereof which is adapted to cooperate with an insertion tool.

Another advantage of the present invention is that the collapsible expanded section can be in the form of a convex shaped head located adjacent the distal tip and includes an annular shaped ring located on a side opposite to said distal tip.

Another advantage of the present invention is that the collapsible expanded section can be in the form of a convex shaped head located adjacent the distal tip and includes convex shaped head includes a second annular shaped outer ring located on a side opposite to said distal tip.

Another advantage of the present invention is that the cross-section diameter of the central member preferably would have a diameter of about 0.3 mm to about 1.2 mm while the outer edge of the collapsible flared section can have a diameter in the order of about 0.5 mm to about 2.2 mm.

Another advantage of the present invention is that the punctum plug or implant can be formed of a nonabsorbable or non-dissolvable material such as silicone, Polytetrafluoroethylene (e.g. Teflon) or other medically compatible non-biodegradable material.

Another advantage of the present invention is that the punctum plug or implant could be formed of an absorbable or dissolvable material to function as a temporary implant. One such absorbable or dissolvable material that could be utilized for practicing this invention is collagen.

Another advantage of the present invention is that the length of the punctum plug can be selected to place the collapsible expanded section in that portion of the canaliculus adjacent the punctum opening or place the collapsible expanded section in the ampula.

Another advantage of the present invention is that a method for treating an external eye condition due to a deficiency of tears using the punctum plug of the present invention which can be used for treating an eye.

BRIEF DESCRIPTION OF THE DRAWINGS

The foregoing and other advantages of this invention will be apparent from the following description of the preferred embodiment of the invention when considered with the illustrations and accompanying drawings which include the following Figures:

FIGS. 21(a), 21(b), 21(c), 21(d1) and 21(e) illustrate the various steps of inserting a punctum plug in the form of the punctum plug illustrated in FIG. 6 through the punctum opening and into the canaliculus.

DESCRIPTION OF THE PREFERRED EMBODIMENT

Figure 1:
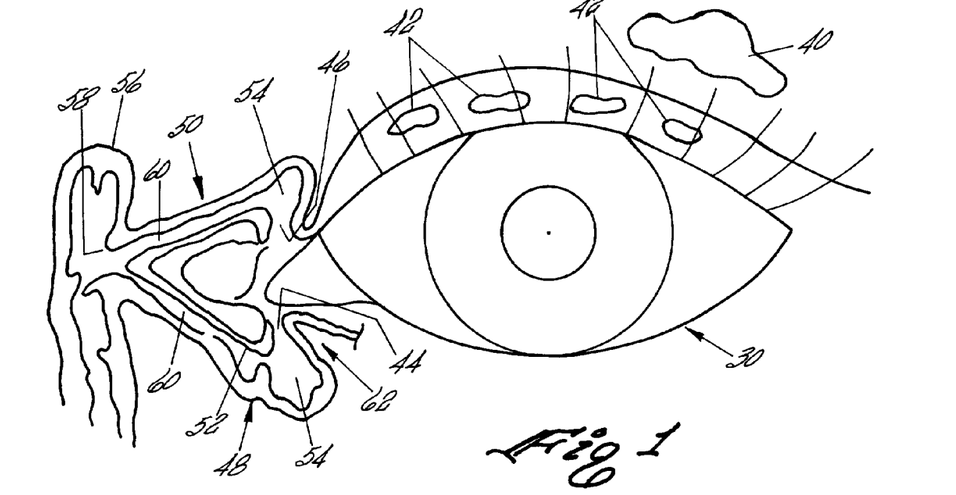
FIG. 1 is a pictorial representation of a lacrimal system of the eye having an upper and lower canaliculus, each of which have a punctum opening, that portion of the canaliculus adjacent the punctum opening, an ampula or sac and a that portion of the canaliculus beyond the ampula or sac.

In order to better understand the teachings of the present invention, and the structure of the eye in its relationship to the present invention, the following brief description of the human eye and the associated lacrimal system illustrated in FIG. 1 and showing the paths of the tears from sources of the tears to the nasal cavity, will first be discussed.

The eye 30 includes a cornea and a pupil which is well known in the art. The source of the tears for the eye is generally classified into "crying tears" and "constant tears". The "crying tears" are produced by a large lacrimal gland 40 illustrated in the upper right hand portion of the illustration of eye 30. The "constant tears" are produced by a series of small glands 42 which are located below the large gland 40 and spaced apart above the cornea of the eye 30. The "constant tears" are the tear secretions which are to be preserved in accordance with the teachings of the present invention.

In the normal eye, approximately 400 drops (9.5 milliliters) of tear secretion are produced during the day and a lesser volume of tear secretion is produced at night during sleep. Tear secretion also protects the eye from infection since the tears contain an enzyme called Lysozyme that functions as an antibiotic. With age, the eye produces less tear secretion, about sixty percent (60%) less at age 65 than at age 18. The tears flow over the eyes and drain through the small openings called the puncta, or punctal openings or punctum openings.

Figure 5:
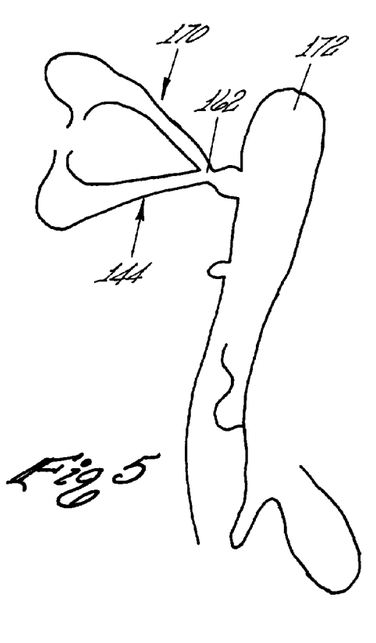
FIG. 5 is a pictorial representation of an anterior and posterior lacrimal system which communicates with an opening in the nasal sac.

There are two punctal openings in the eye, a lower punctum 44 and an upper punctum 46. The punctal openings 44 and 46 form openings into the corresponding a lower canaliculus 48 and an upper canaliculus 50. Each of the punctal openings 48 and 50 have a fibrous tissue ring, illustrated as 52, formed therearound. The fibrous tissue ring 52 is a fairly dense relatively avascular connective ring of tissue. The lower canaliculus 48 and the upper canaliculus 50 are connected to a lacrimal sac 56. The lacrimal sac 56 is connected to a nasal lacrimal duct 58. The lacrimal duct 58, in turn, extends into the nasal cavity as illustrated in FIG. 5. The tears produced by the eye travel through the punctal openings, through their associated canaliculus.

As the tears exit the lower canaliculus 48 and the upper canaliculus 50, the tear flows merge in the lacrimal duct 58 and then travel to the nasal cavity. Lower canaliculus 54 and the upper canaliculus 50, which comprise the drainage channels of the eye travel to the nasal cavity. Lower canaliculus 48 and the upper canaliculus 50, which comprise the drainage channels of the eye travel to the nasal cavity. Lower canaliculus 48 and the upper canaliculus 50, which comprise the drainage channels of the eye are connected to an ampula or sac, shown generally as 54, which has a dimension of about 2 mm to 3 mm at its widest portion. The ampula or sac 54 forms part of an narrows into the horizontal portion of the canaliculus, shown generally as 60.

The medial position of the horizontal portion of the canaliculus has a diameter in the order of about 0.5 mm and an overall length of about 8 mm. In practicing the present invention, the punctum plug or implant is passed through that portion of the canaliculus located between the punctum opening 44 and into the ampula 54 comprising a portion of the horizontal canaliculus 60.

It has developed that mechanism of lacrimal drainage results in the drainage of tear flow from the eye. One article which describes this phenomenon is entitled "*BLINKING AND THE MECHANICS OF THE LACRIMAL DRAINAGE SYSTEM*" by Marshall G. Doane, Ph.D., which appeared in OPHTHALMOLOGY, Volume 88, No. 8, August 1981, pages 844 through 851 inclusive (the "Doane Article"). The Doane Article describes that during each blink cycle, the upper lid sweeps down over the eye. As the lid descends, the papillae containing the punctal opening elevate from the medial lid margin. As the lid continues to descend, the puncta are occluded by the contact of the lid margins. Further lid closure squeezes the canaliculi and sac forcing the tear or contained fluid to drain into the nasolacrimal duct.

At the end of a complete lid closure, the lacrimal system is compressed and largely empty of fluid. During the opening phase, the puncta are still occluded. The walls of the passage ways or canaliculus expand by elastic force causing a partial vacuum or suction. As the lid continue to open, the puncta "pop" apart, and excess tear fluid is immediately drawn off the eye into the canaliculus.

The insertion of an implant into the ampula of the canaliculus tends to retard the squeezing action of the canaliculi during eyelid closure and to reduce the partial vacuum during eyelid opening which results in a larger quantity of tear fluid remaining on the eye. If medication is added to the eye, it remains on the eye longer thereby effecting the eye treatment by the medication which, otherwise, would be removed by the blinking and the mechanics of the lacrimal drainage system.

Figure 2A:
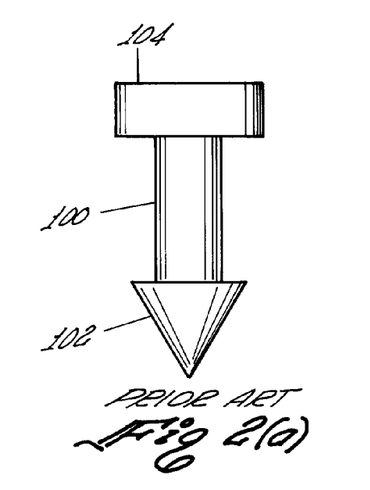
FIG. 2(a) is a pictorial representation in cross-section of a prior art Freeman punctum plug implanted in the punctum opening and in that portion of the canaliculus adjacent the punctum opening.

The prior art Freeman punctum plug illustrated in FIG. 2(a) has a body 100, a barbed shaped distal end 102 and a rectangular top 104 and is adapted to be implanted in the punctum opening and in that portion of the canaliculus adjacent the punctum opening.

Figure 2B:
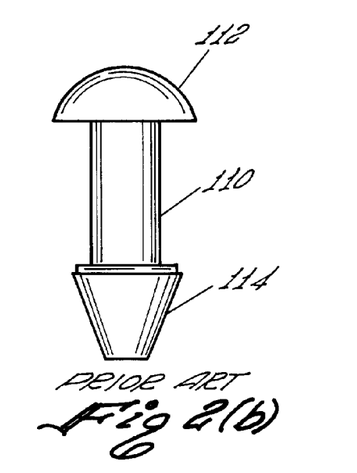
FIG. 2(b) is a pictorial representation in cross-section of another prior art Freeman punctum plug implanted in the punctum opening and in that portion of the canaliculus adjacent the punctum opening.

The prior art Freeman punctum plug illustrated in FIG. 2(b) having an elongated central member 110, a dome-shaped top 112 and a truncated distal tip 114 is adapted to be implanted in the punctum opening and in that portion of the canaliculus adjacent the punctum opening.

Figure 3:
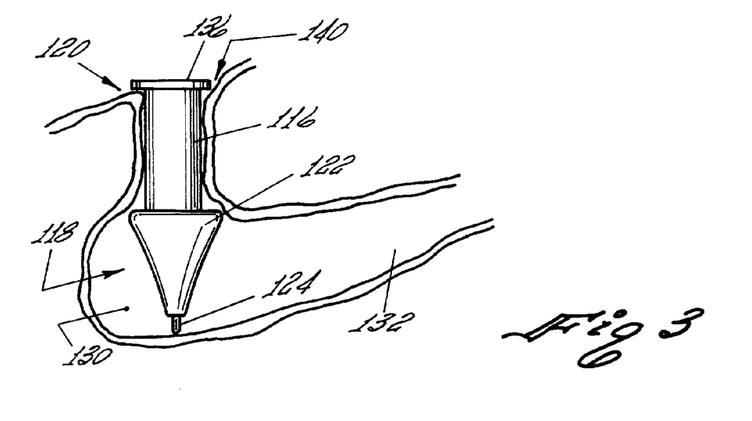
FIG. 3 is a pictorial representation of a punctum plug having a collapsible expanded section which terminates in a distal tip which is substantially co-axial with the central axis of the elongated body located within the ampula which forms part of the horizontal portion of the canaliculus.

The prior art Herrick punctum plug illustrated in FIG. 3 has an elongated body 116 having a pair of spaced ends 118 and 120 and a collapsible expanded section 122 located between the ends 118 and 120. The end 118 terminates in a distal tip 124 which is substantially co-axial with the central axis of the elongated body 116 located within the ampula 130 which forms part of the horizontal portion of the canaliculus 132. The end 120 terminates in a thin retaining lip 136 which extends in an anterior direction and which is adapted to be oriented to extend beyond the edge of the punctum opening 140 and to engage the lip margin defining the eyelid implanted in the punctum opening and in that portion of the canaliculus adjacent the punctum opening 140.

Figure 4:
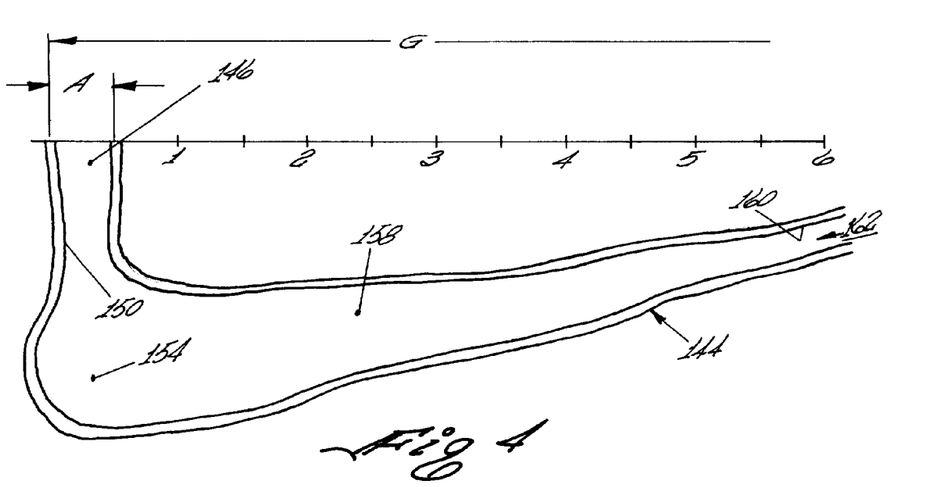
FIG. 4 is a diagrammatic representation of a canaliculus which extends from the punctum opening, that portion of the punctum opening adjacent the punctum opening, the ampula or sac, that portion of the canaliculus extending beyond the ampula or sac and the medial opening thereof into the nasal sac.

FIG. 4 is a diagrammatic representation of a canaliculus shown generally as 144 which extends from the punctum opening 146, through that portion of the canaliculus 150 adjacent the punctum opening and into the ampula or sac 154 and into that portion of the canaliculus 158 extending beyond the ampula or sac 154 and the medial opening 160 thereof into the nasal sac shown generally as 162.

The table set forth below sets forth some typical dimensions of the lacrimal system illustrated and described in connection with FIG. 4.

DIMENSIONS OF ELEMENT
OF A TYPICAL LACRIMAL SYSTEM
TABLE OF DIMENSIONS OF LACRIMAL APPARATUS

| Element | Anatomical Name/Description | Typical Range |
|---|---|---|
| 146 | Punctum opening | .3 mm to .8 mm |
| 150 | Canaliculus extending form Punctum Opening | 2.0 mm to 2.5 mm |
| 154 | Ampula or horizontal sac of horizontal canaliculus | 1.0 mm to 3.0 mm |
| 158 | Reduced opening of horizontal canaliculus | .5 mm to .6 mm |
| 144 | Length of horizontal canaliculus | 7.5 mm to 8.5 mm |

In the pictorial representation of FIG. 5, an anterior lacrimal system 170 and posterior lacrimal system 144 communicate with opening 162 in the nasal sac 172. The relative size of the lacrimal system to the size of the nasal sac discloses that the nasal sac is larger. Of importance, however, is that the general shape and configuration of the lacrimal system and the nasal sac, from an anatomically aspect, disclose that the structure thereof are quite similar.

Figure 6:
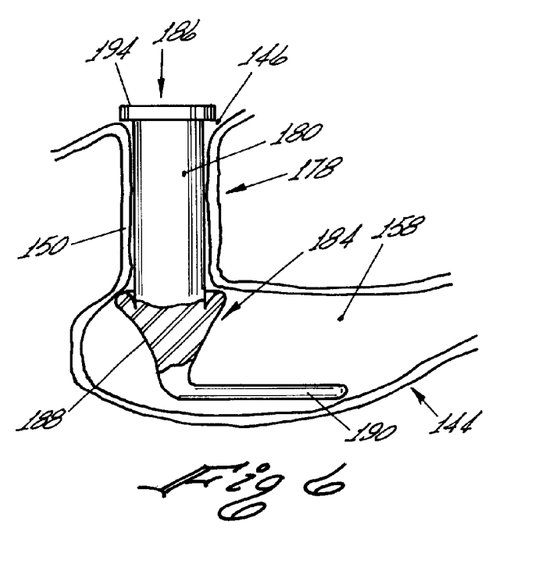
FIG. 6 is a pictorial representation in cross-section of a punctum plug incorporating the teachings of this invention implanted in the punctum opening and in that portion of the canaliculus adjacent the punctum opening with an elongated distal section located in the ampula or sac.

In FIG. 6, the cross-section of a punctum plug 178, incorporating the teachings of this invention, discloses that the punctum plug or implant comprises an elongated member 180 having central axis and a pair of spaced ends 184 and 186. One of the pair of ends, end 184, includes a distal section 188 which terminates in an elongated distal tip 190 which extends in a direction substantially normal or perpendicular to the central axis of the elongated member 180. The elongated member 180 and the elongated distal tip 190 are formed of a dimension to pass through a punctum opening 146 and into the canaliculus 158 of an eye.

In FIG. 6, the distal section, forming one end 184, is illustrated, in the preferred embodiment, to be a collapsible expanded section and the other of the pair of ends 186 includes a thin retaining or elongated lip 194. For purpose hereof, the term "thin elongated lip" means an extension or lip which extends or protrudes beyond the outer surface of the elongated member and which would position the thin elongated lip anterior and away from the cornea. The thin retaining or elongated lip 194 is positioned on the elongated member 180 to position the thin elongated lip 194 to extend in a generally anterior direction upon insertion of the same into a punctum opening 146.

In FIG. 6, the punctum plug 178 is illustrated as being implanted in the punctum opening 146 and in that portion of the canaliculus 150 adjacent the punctum opening with the elongated distal section 188 located in the ampula or sac and the elongated distal tip 190 extending through the reduced opening 158 into the canaliculus 144.

Figures 7, 8:
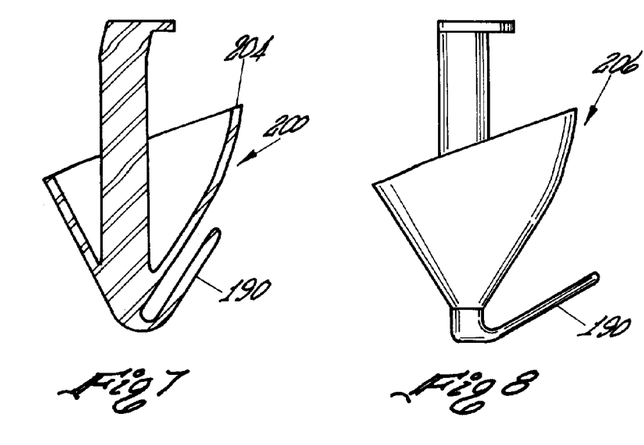
FIG. 7 is a pictorial representation partially in cross-section of another embodiment of a punctum plug incorporating the teachings of this invention where the collapsible extended section has a sloping outer edge and terminate in an elongated distal starting tip which extends substantially normal or perpendicular to the axis of the elongated body which is deflected at the second end thereof.
FIG. 8 is a front elevational view of yet another embodiment similar to that illustrated in FIG. 8 wherein the elongated body is substantially straight.

FIG. 7 is a pictorial representation partially in cross-section of another embodiment of a punctum plug 200 incorporating the teachings of this invention where the collapsible extended section has a sloping outer edge 204 and terminates in an elongated distal starting tip 190 which extends substantially normal or perpendicular to the axis of the elongated body which is deflected at the second end thereof.

FIG. 8 is a front elevational view of yet another embodiment 206, which is similar to that illustrated in FIG. 8, wherein the elongated body is substantially straight.

Figure 9:
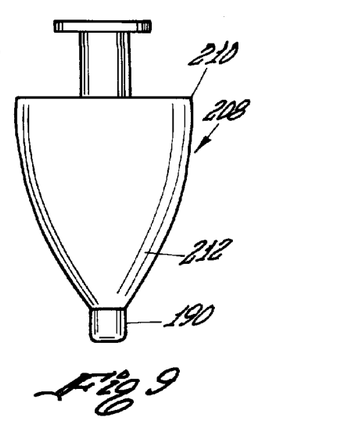
FIG. 9 is a left side plan view of still yet another embodiment similar to that illustrated in FIG. 8 wherein the elongated body is substantially straight and the outer edge of the collapsible expanded section is substantially planar.

FIG. 9 is a left side plan view of still yet another embodiment 208 similar to that illustrated in FIG. 8 wherein the elongated body is substantially straight and the outer edge 210 of the collapsible expanded section 212 is substantially planar.

Figure 10:
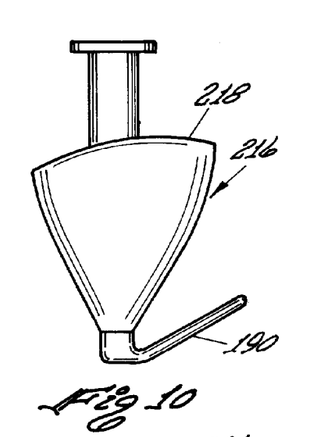
FIG. 10 is a front elevational view of a punctum plug similar to that illustrated in FIG. 8 wherein the outer edge has a slight upward curve.

FIG. 10 is a front elevational view of a punctum plug 216 similar to that illustrated in FIG. 8 wherein the outer edge 218 has a slight upward curve.

Figure 11:
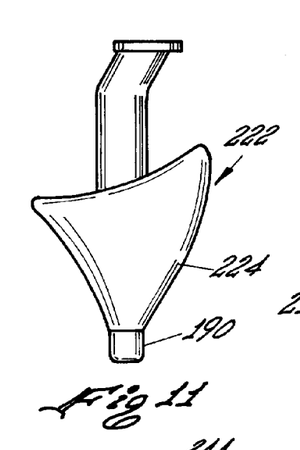
FIG. 11 is a left side plan view of a punctum plug similar to that illustrated in FIG. 7 having a non-uniform shaped collapsible expanded section.

FIG. 11 is a l eft side plan view of a punctum plug 2 22 similar to that illustrated in FIG. 7 having a non-uniform shaped collapsible expanded section 224.

Figure 12:
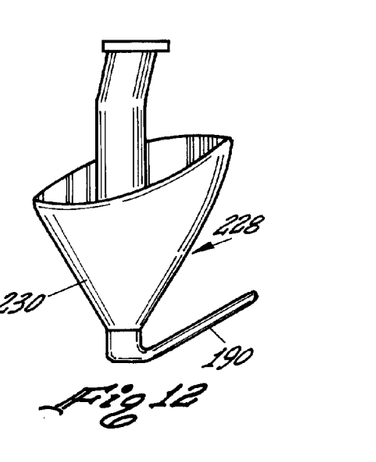
FIG. 12 is a front elevational view of a punctum plug similar to that illustrated in FIG. 7 having a non-uniform shaped collapsible expanded section.

FIG. 12 is a front elevational view of a punctum plug 228 similar to that illustrated in FIG. 7 having a non-uniform shaped collapsible expanded section 230.

Figure 13:
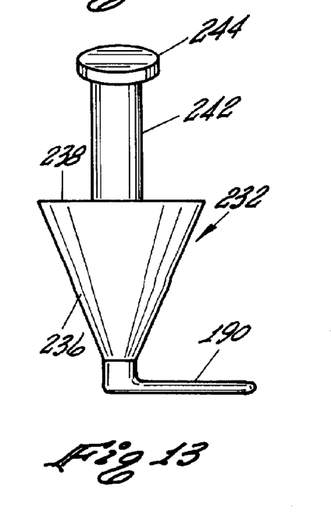
FIG. 13 is a front elevational view of a punctum plug having a collapsible expanded section in the form of a collapsible flared section having a planar outer edge and a second end which is deflected at a slight angle to position the thin elongated lip anterior to the cornea of an eye.
Figures 14, 15, 16:
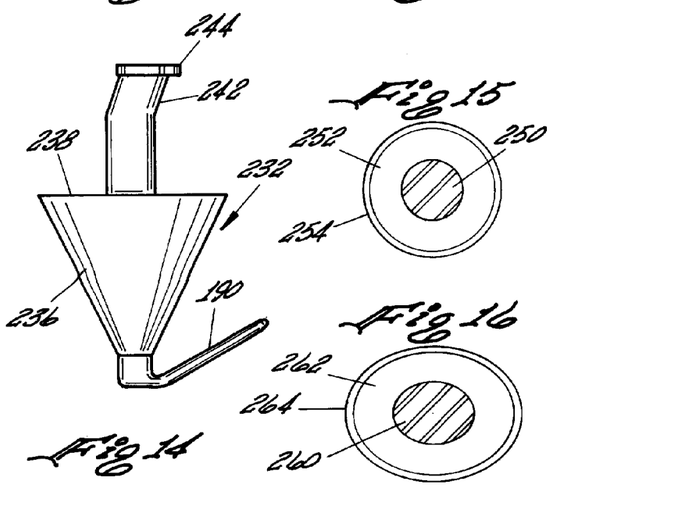
FIG. 14 is rotated front elevational view of the embodiment of the punctum plug illustrated in FIG. 13 illustrating the relationship between the second end and the thin elongated lip.
FIG. 15 is a pictorial representation, in cross-section, showing an embodiment wherein the cross-section of the central member and outer edge of the collapsible flared section are both circular.
FIG. 16 is a pictorial representation, in cross-section, showing an embodiment wherein the cross-section of the central member and outer edge of the collapsible flared section are both oval.

FIGS. 13 and 14 illustrate in a front elevational view and rotated view a punctum plug 232 having a collapsible expanded section in the form of a collapsible flared section 236 having a planar outer edge 238. The second end 242 is deflected at a slight angle to position the thin elongated lip 244 anterior to the cornea of an eye. For purposes hereof, the term "thin elongated retaining lip" means an extension or lip which extends or protrudes beyond the outer surface of the elongated member and which would be located around approximately 300° or less of the periphery of the elongated member leaving the posterior surface thereof free from protruding into, or from contacting with or abrading the surface of the eye including the cornea or conjunctiva.

FIG. 14 clearly illustrated the relationship between the second end 242 and that the slight angle thereof supports the thin elongated lip 244 anterior of the cornea of an eye.

In FIG. 15, the cross-section of the elongated central member 250 and outer edge 254 of the collapsible flared section 252 are both circular.

In FIG. 16, the cross-section of the central member 260 and outer edge 264 of the collapsible flared section 262 are both oval.

Figures 17, 18, 19:
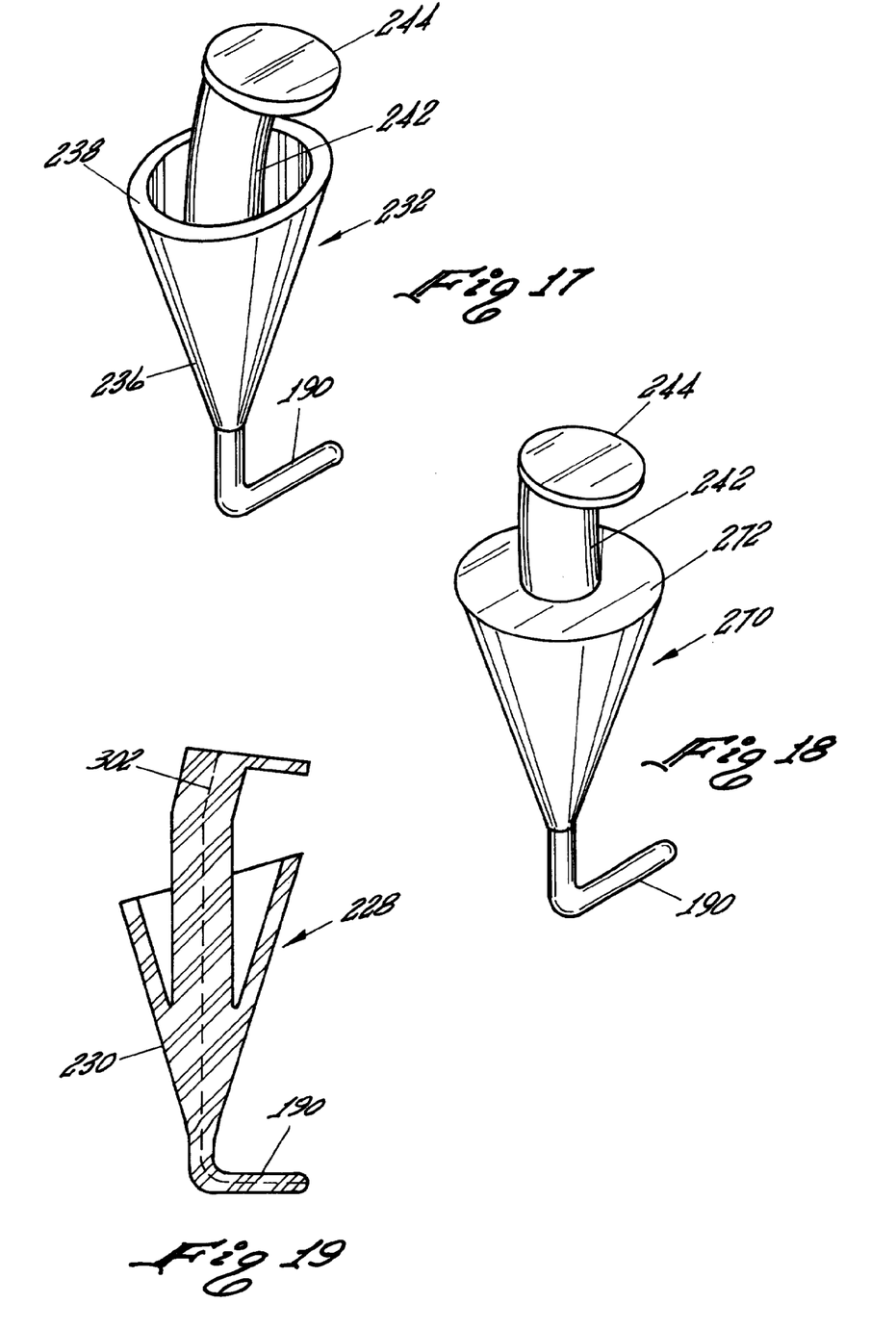
FIG. 17 is a front top and left side perspective view of the punctum plug illustrated in FIGS. 13 and 14.
FIG. 18 is a front top and left side perspective view of the punctum plug similar to that illustrated in FIG. 17 except that the collapsible expanded section is formed of a material which is compressible.
FIG. 19 is a cross-sectional view of the punctum plug illustrated in FIG. 12.

In the front, top and left side perspective view of the punctum plug 232 illustrated in FIG. 17, which corresponds to the punctum plug 232 illustrated in FIGS. 13 and 14, the slight angle of the second end 242 positioned the thin elongated lip 244 anterior of the cornea of the eye. The elongated distal tip 190, which is substantially normal or perpendicular to the axis of the elongated body, id likewise substantially normal to he thin elongated lip 244. When the punctum plug 232 is implanted, the elongated distal tip 190 is oriented so to be located with the canaliculus urging and supporting the thin elongated lip 244 in a position to enable the same to engage and be supported by the margin of an eyelid.

In FIG. 18, the front, top and left side perspective view of the punctum plug 270 is similar to that illustrated in FIG. 17 with respect to second end 242 and thin elongated lip 244 except that the collapsible expanded section 272 is formed of a material which is compressible. This results in a punctum plug which compresses upon insertion as opposed to being collapsed as is the case for punctum plug 232 illustrated in FIG. 17.

FIG. 19 is a cross-sectional view of the punctum plug 228 with the elongated distal tip 190 as illustrated in FIG. 12.

Figure 20:
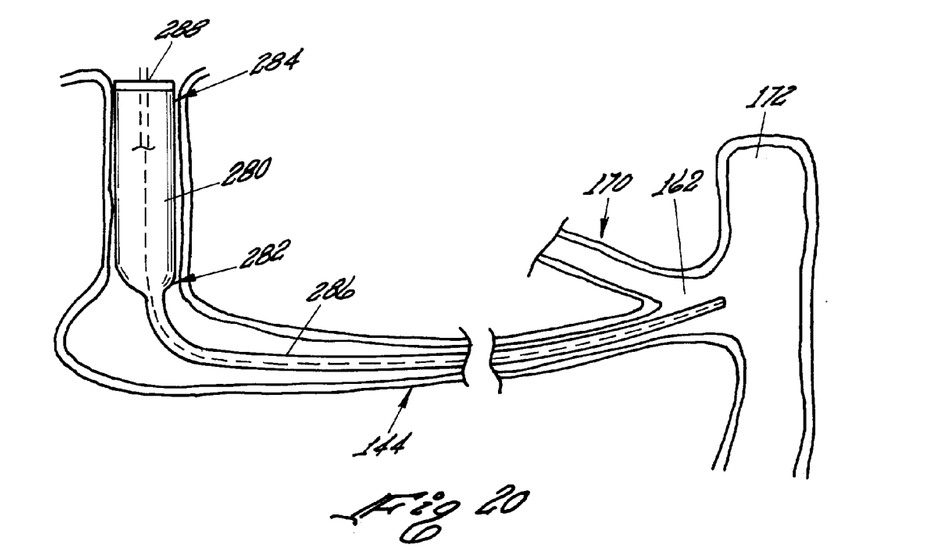
FIG. 20 is a pictorial representation of a punctum plug of the present invention used as an anchor for a stent to repair canalicular lacerations and to block fluid flow through a canalicular canal.

FIG. 20 is a pictorial representation of a punctum plug 284 having a first end 282 having a very elongated distal tip 286 and a second end 284 having a thin elongated lip 288 wherein the elongated substantially perpendicular distal tip 286 is used as an anchor for a stent to repair canalicular lacerations and to block fluid flow through a canalicular canal. The stent defined by the elongated distal tip 286 passes into the opening 162 and the tip may just slightly extend into the nasal sac 172. The elongated distal tip 286 terminates in a distal starting tip having a sloped surface sloped towards the starting tip as shown in FIG. 20.

In utilizing the punctum plug or implant for practicing the teaching of the invention, the eye surgeon can utilize any one of a number of methods for determining if an external condition due to a deficiency of tears exists. In the preferred embodiment of the present invention, the canaliculus can be temporarily occluded by placing a temporary implant (which may be a temporary punctum plug or canalicular implant) to provide a temporary blockage of the punctum opening or canaliculus as the case may be. By utilizing a temporary implant for providing temporary blockage, the eye surgeon can observe the response of the patient to the temporary blockade. If an improvement in the eye condition of the patient is noted, a permanent punctum plug or implant can be implanted within the punctum opening and vertical portion of the canaliculus or ampula of the patient.

It is envisioned that the temporary implant used in practicing the invention can be in the form of one of the embodiments described hereinbefore. If a punctum plug or implant is to function as a temporary implant to provide temporary blockage of the punctum opening or vertical portion of the canaliculus, the temporary implant can be fabricated from a medically acceptable, dissolvable biodegradable material such as collagen, catgut, biodegradable suturing material, polyglycolic acid or the like. The temporary punctum plug or implant can be inserted into the punctum opening and vertical portion of the canaliculus and/or ampula utilizing the procedures set forth hereinbelow in FIGS. 21(a) through 21(e).

If the eye surgeon determines that a permanent occlusion of the punctum opening and vertical portion of the canaliculus is desirable, a permanent punctum plug or implant can be utilized as a means for providing a permanent occlusion of the punctum opening and the vertical portion of the canaliculus. In such event, the permanent punctum plug or implant can be fabricated from a non-biodegradable material or material and one which is not absorbable by or dissolved in the human body. Examples of such materials are medical grade rubber, silicone, polyethylene, polypropylene, polytetrafluoroethylene (e.g. Teflon) are some of the materials. The diameter of the elongated member of the punctum plug would be in the order of about 0.2 mm to about 1.2 mm and the overall length could be in the order of about 2.5 mm to about 8 mm. The preferred diameter for elongated member of the punctum plug is in the order of about 0.5 mm to about 1.0 mm. Referring now to the pictorial representations of FIGS. 21(a) through 21(e)

FIGS. 21(a) through 21(e) illustrate the method for inserting the punctum plug illustrated in FIG. 13, 14 and 17 into the punctum opening 146 and into that portion of the canaliculus extending from the punctum opening 146 into communication with the ampula 154 forming part of the horizontal canaliculus 144.

In FIGS. 21(a) through 21(e), the pictorial representations are shown based upon the punctum plug 232 being inserted into the punctum opening 146, through that portion of the canaliculus shown as 150 and into the canaliculus 144.

In connection with the punctum plug 232 illustrated in FIGS. 21(a) through 21(e), the length of the punctum plug 232 and the length of the elongated distal tip 190 can be selected to place the collapsible flared section 236 into the ampula 154.

Of course, the punctum plug 232 could be inserted into the upper canaliculus 50 in a similar manner as that described below.

Figure 21A:
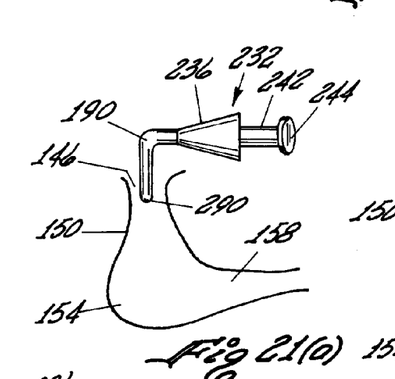

As illustrated in FIG. 21(a), the elongated distal tip 190 is positioned with the distal starting tip 290 penetrating the punctal opening 146 such that the elongated distal tip 190 will gently expand the fibrous ring defining the punctal opening 146.

Figure 21B:
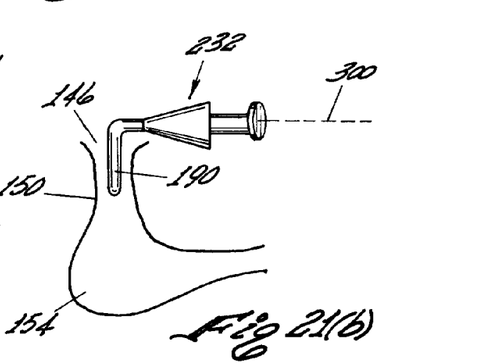

In FIG. 21(b), the elongated distal tip 190 is passed through the punctal opening 146 and is directed towards the ampula 154.

Figures 21C, 21D:
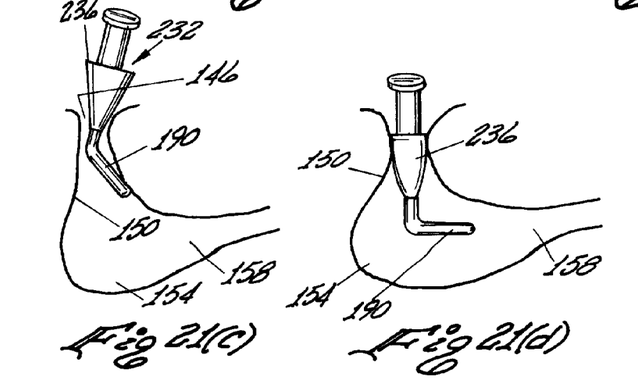

In FIG. 21(c), the punctum plug 232 is rotated urging the collapsible flared section 236 through the punctal opening 146 until the punctal opening 146 engages the exterior surface of the collapsible flared section 236.

FIG. 21(c) illustrates that the punctum opening 146 slideably engages the collapsible flared section 236 as an insertion force is applied to the punctum plug 232. A radial force is developed around the surface of the collapsible flared section 236 as the punctum plug 30 slideably moves past the punctum opening 146. A radial force is applied to the collapsible flared section 236 in a direction so as to cause the collapsible flared section to be urged into its collapsed position. A clamping force is developed between the outer walls of the collapsed conical-shaped member defining the collapsible flared section 236 and the inner walls of section 150 of the canaliculus.

In FIG. 21(d), the collapsible expanded section 236 is illustrated as entering into the ampula 154 orienting the elongated distal tip 190 towards the reduced opening 158.

Figure 21E:
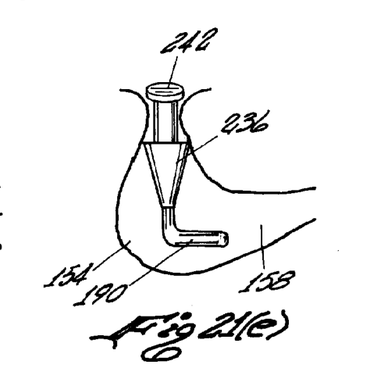

FIG. 21(e) illustrates the fully inserted punctum plug 232 has the collapsible expanded section 236 positioned with the ampula 154 and the portion 150 of the canaliculus is occluded. the elongated distal tip 190 extends into the reduced opening 158 to position the thin elongated lip 242 in contact with and against the margin of the eye.

By utilizing the teachings of the present invention, a method for treating external eye conditions due to a deficiency of tears is disclosed. The method includes the steps of testing the eye to determine if a tear deficiency exists; and, if a tear deficiency is determined, placing a punctum plug having an elongated member, a first end and a second end wherein the first end has a thin retaining lip and a second end having a distal section, which in the preferred embodiment is a collapsible flared section, within the punctum opening and that portion of the canaliculus located between the a punctum opening and ampula.

The present invention also teaches a method for inserting an implant through a punctum opening into that portion of at least one of the canaliculi having interior side walls of an eye extending between the punctum opening and the ampula which is part of the horizontal canaliculus for treating external eye condition due to a deficiency of tears. The method comprises the steps of inserting a punctum plug having an elongated central member and a pair of ends wherein one end of said pair of ends has a distal section, which may be in the form of a collapsible flared section, terminating in an elongated distal tip having a distal starting tip and the other of said pair of ends has a thin retaining lip and wherein the starting tip and collapsible flared section pass through the punctum opening and into that portion of the canaliculus located between the punctum opening and the ampula of at least one of the canaliculi interior of the eye causing the collapsed flared section to be collapsed as it passes through the punctum opening and that portion of the canaliculus communicating with the punctum opening and to return to its extended position within the ampula to occlude the punctum opening and that potion of the canaliculus communicating with the punctum opening.

The step of urging in the above described method can include using an insertion tool, illustrated by dashed line 300 in FIG. 21(b), which is inserted into the second end to apply force to urge the punctum plug through the punctum opening, through that portion of the canaliculus communicating with the punctum opening and into the ampula.

The punctum plug or implant of the present invention utilizes the collapsible flared section for occluding the punctum opening and the canaliculus, and the punctum plug is held in place by the thin elongated tip at the second end being urged against the margin of the eye and the elongated distal tip which extends into the reduced opening of the horizontal canaliculus. By selecting a punctum plug of an appropriate length, the above elements are effective to hold the plug in place and to prevent inadvertent removal or any possible migration of the plug while implanted within the eye.

The punctum plug of the present invention is preferably used as a permanent implant for practicing the invention. In the method disclosed and taught herein, the temporary implant could be an implant well known in the art, could be a means for occluding the punctum opening and the canaliculus, could be a temporary implant as disclosed in the prior art section above or any other means known in the art for temporarily occluding the eye to determine if an improvement in eye condition is noted. However, the temporary implant could, likewise, be a punctum plug or implant having a structure disclosed herein wherein the implant is formed of an absorbable or dissolvable (in the body) biodegradable material. The permanent punctum plug or implant can be identical in shape, size and dimension but be formed of a non-biodegradable, nonabsorbable or non-dissolvable (in the body) material. The advantage of utilizing a temporary implant and a permanent implant which has a structure as disclosed herein is that the collapsible flared section of the canalicular implant performs the function of occluding the punctum opening and/or the canaliculus. If the punctum plug does not extend all the way into the ampula and remains within the punctum opening and the that portion of the canaliculus which communicates with the punctum opening, the collapsible flared section develops a clamping pressure between the collapsible flared section and the interior walls of the punctum opening or the canaliculus while providing the desired blockage to the eye.

If it is desirable to have a small passageway available to enable a limited flow of tears to pass through the occlusion, it is envisioned that the punctum plug or implant could have an aperture extending axially through the center thereof. For example, the punctum plug could have a lacrimal fluid control opening, such as shown by dashed line opening 302 in FIG. 19, to provide a passageway of a predetermined diameter to control tear secretion flow or, the alternative, a slot could be formed around the periphery thereof to facilitate a partial tear flow.

It is also envisioned that the punctum plug or implant of the present invention could include material which is responsive to actinic radiation, such as for example X-rays, so that the eye surgeon can perform tests to determine if the punctum plug or implant is properly located within the punctum opening and the canaliculus. One such material that can be utilized is barium, in appropriate concentrations known to persons skilled in the art, so as to be responsive to actinic radiation, such as X-rays. The use of such materials responsive to actinic radiation is of such a low enough level that it does not cause any adverse effects to the patient into which a punctum plug or implant containing the same is implanted.

Typical dimensions for the punctum plug may include the elongated member having a diameter of about 0.5 mm to about 1.2 mm. The diameter of the outer ring defining the outer edge of the collapsible flared section may be on the order of about 1.5 mm to about 2.5 mm. The overall length of the implant could be about 2.5 mm to about 8 mm.

The diameter of the distal starting tip can be about 0.2 mm to about 0.4 mm with about 0.3 mm being preferred.

The length of the elongated distal tip could be in the range of about 1.5 mm to about 3.0 mm The preferred embodiments and the various shapes, sizes and design for the punctum plug or implants disclosed herein are exemplary, and all variations thereof are contemplated to be within the teaching of and scope of this invention.

What is claimed is:

1. An implant comprising
an elongated member having a central axis and a pair of spaced ends wherein one of said pair of ends includes a distal section terminating in an elongated distal tip which extends in a direction substantially normal to the central axis and the other of ends includes a thin elongated retaining lip, said thin elongated retaining lip being positioned on the elongated member to position the elontated tip to extend in a generally anterior direction upon insertion into a punctum opening, said elongated member and said elongated distal tip being formed of a dimension to pass through a punctum opening of an eye.

2. The implant of claim 1 wherein said one of said pair of ends includes a collapsible expanded section.

3. The implant of claim 2 wherein said collapsible expanded section is a collapsible flared section which is collapsible relative to said central axis in response to the application of a force on the collapsible flared section in a direction to collapse the same and urge the collapsible flared section into a collapsed position.

4. The implant of claim 3 wherein said collapsible flared section defines a substantially uniform shape for enabling said collapsible flared section to be uniformly collapsed relative to said central axis.

5. The implant of claim 4 wherein said collapsible flared section defines an outer edge.

6. The implant of claim 5 wherein said collapsible flared section has a substantially circular shaped outer edge.

7. The implant of claim 2 wherein the elongated member curves slightly in a direction towards said other of said pair of ends.

8. The implant of claim 2 wherein said collapsible expanded section has a substantially uniform shape for enabling said collapsible expanded section to be uniformly collapsed relative to said central axis.

9. The implant of claim 2 wherein said collapsible expanded section is a collapsible flared section having a hollowed out central area defining a thin-walled, conical shaped member.

10. The implant of claim 1 having a fluid control opening extending therethrough to pass lacrimal fluid.

11. The implant of claim 10 wherein said fluid control opening is selected to have a predetermined diameter to control the flow of lacrimal fluid passed therethrough.

12. The implant of claim 11 wherein said fluid control opening has a diameter in the range of about 0.10 mm to about 0.40 mm.

13. The implant of claim 2 wherein said collapsible expanded section has is shaped for enabling said collapsible expanded section to be collapsed relative to said central axis.

14. The implant of claim 2 wherein said collapsible expanded section is convex shaped.

15. The implant of claim 1 wherein said distal tip terminates in a starting tip having a dimension to pass through the punctum opening.

16. A punctum plug comprising
an elongated central member having a central axis and a pair of ends wherein one of said pair of ends includes means defining a collapsible flared section terminating in a distal starting tip which extends substantially normal to the central axis and having a dimension to pass through a punctum opening, said collapsible flared section being collapsible relative to said central axis in response to the application of force on the collapsible flared section in a direction to collapse the same and urge the collapsible flared section into a collapsed position and the other of said pair of ends includes a thin elongated retaining lip having a section which extends in an anterior direction upon insertion of the implant and which engages a lip margin of an eye, said elongated central member, and said collapsible flared section being formed of a dimension to pass through a punctum of an eye.

17. An implant comprising
an elongated central member having a central axis, a first end and a second end, said first end having a thin elongated retaining lip having a section which extends in an anterior direction upon insertion of the implant and which engages a lip margin of an eye and said second end having an elongated distal tip which extends substantially normal to the central axis, said elongated central member and said elongated distal tip being formed of a dimension to pass through a punctum of an eye.

18. The implant of claim 17 wherein said second end further includes a collapsible flared section having a preselected shape and wherein said collapsible flared section is adapted to be collapsible relative to said central axis in response to the application of force on the collapsible flared section in a direction to collapse the same and urge the collapsible flared section into a collapsed position and wherein said collapsible flared section has a substantially circular cross-section.

19. The implant of claim 18 wherein said collapsible flared section has an initial cross-sectional dimension at said second end which is substantially equal to said predetermined cross-sectional dimension and which increases in cross-sectional dimension as said collapsible flared section extends towards said first end.

20. The implant of claim 19 wherein said collapsible flared section terminates in an outer edge.

21. The implant of claim 20 wherein said collapsible flared section and said outer edge are annular shaped and wherein said collapsible flared section is responsive to a force applied in direction to collapse the same to urge the collapsible flared section into a collapsed position.

22. The implant of claim 17 wherein said distal tip has a cross-sectional area which is smaller in cross-sectional dimension than said elongated central member.

23. The implant of claim 17 wherein said elongated distal tip terminates in a distal starting tip having a sloped surface sloped towards the starting tip.

24. The implant of claim 17 wherein said elongated central member has a tool receiving opening.

25. The implant of claim 24 wherein said tool receiving opening extends from a location adjacent said second end, through the elongated central member and through said first end.

26. A punctum plug comprising
an elongated member having a central axis, first end, a second end and a central section extending between said first end and said second end;
said pair of ends said first end includes a thin elongated retaining lip, said thin elongated retaining lip being positioned on the elongated member to position the elontated tip to extend in a generally anterior direction upon insertion into a punctum opening,
said second end having a collapsible expanded section which varies in cross-section as the collapsible expanded section approaches the first end, said collapsible expanded section having an elongated distal tip which extends substantially perpendicular to said central axis, said collapsible flared section being responsive to the application of a force in a direction to collapse the same by being urged into its collapsed position.

27. The implant of claim 26 wherein the elongated distal tip terminates in a tip insertion section having a distal starting tip.

28. The implant of claim 27 wherein the diameter of the distal starting tip is about 0.2 mm to about 0.4 mm.

29. The implant of claim 28 wherein the diameter of the distal starting tip is about 0.3 mm.

30. The implant of claim 26 wherein the cross-section of the central member is generally circular in shape.

31. The implant of claim 30 wherein the diameter of the generally circular shaped central member is between about 0.7 mm to about 1.0 mm.

32. The implant of claim 26 wherein said collapsible expanded section is convex.

33. The implant of claim 32 wherein the diameter of the collapsible expanded section is on the order of about 1.5 mm to about 2.0 mm.

34. The implant of claim 26 wherein the overall length of the implant is about 2.5 mm to about 8 mm.

35. The implant of claim 26 wherein said collapsible expanded section is in the form of a collapsible flared section having a hollowed-out central area defining a thin-walled, conical-shaped member.

36. The implant of claim 26 wherein the implant is formed of a biodegradable material.

37. The implant of claim 36 wherein the biodegradable material is a collagen material.

38. The implant of claim 26 wherein the implant is formed of a non-biodegradable material.

39. The implant of claim 38 wherein the non-biodegradable material is a silicone material.

40. An implant adapted to be inserted into a punctum opening of an eye and be transported therethrough into the ampula to occlude the canaliculus, said implant comprising an elongated member having a first end and a spaced, opposed second end and a central member having a predetermined cross-sectional dimension extending from said first end to said second end;

said first end includes a thin elongated retaining lip, said thin elongated retaining lip being positioned the elongated member to position the elontated tip to extend in a generally anterior direction upon insertion into a punctum opening, said second end having a collapsible expanded section which varies in cross-section as the collapsible expanded section approaches the second end and which terminates in an outer edge having a dimension which is greater than the predetermined cross-sectional dimension of the central member, said collapsible expanded section having an extended distal section which extends in a direction substantially normal to the central axis, said collapsible expanded section having a geometrical dimension approximately equal to that of the punctum opening of an eye adapted to pass the same, and wherein the application of a radial force in a direction to collapse the collapsible expanded section urges the same from its extended position into its collapsed position.

41. The implant of claim 40 wherein the elongated member has a slightly angular curve in a selected direction causing the first end to be slightly deflected relative to the second end for orienting and urging the section which extends in an anterior direction into holding engagement with the punctum opening and lip margin.

42. A method for treating an external eye condition due to a deficiency of tears including the steps of testing the eye to determine if a tear deficiency exists; and if a tear deficiency is determined to exist, inserting into the punctum opening an implant having an elongated central member and a pair of ends wherein one end of said pair of ends has a distal section terminating in an elongated distal section which is extends substantially normal to the central axis and which terminates in a distal starting tip and the other of said pair of ends has a thin elongated retaining member, and wherein the elongated distal section including the distal starting tip and the collapsible expanded section pass through the punctum opening and into the canaliculus of an eye.

43. A method for inserting a punctum plug through a punctum opening having interior side walls and into the canaliculus of an eye for treating an external eye condition due to a deficiency of tears comprising the steps of inserting a punctum plug including an elongated central member having a central axis, a first end and a second end wherein the first end has a this elongated retaining lip adapted to engage the exterior of the punctum opening and the lip margin and wherein the second end has a collapsible flared section having an elongated distal tip which extends substantially normal to the central axis, said distal tip of said second end passing through the punctum opening transporting the collapsible flared section in its extended position to the punctum opening; and urging the distal tip of said second end through the punctum opening and into the canaliculus to transport the collapsible flared section through the punctum opening and into the canaliculus wherein said collapsible flared section slideably engages the interior side walls of the canaliculus to apply a radial force against the collapsible flared section urging the same into its collapsed position;

transporting the elongated central member and the collapsible flared section completely through the punctum opening into the canaliculus wherein the radial force is no longer applied against the collapsible flared section and the collapsible flared section then reverts back to its substantially extended position to occlude the punctum opening and the canaliculus; and positioning the lip over the punctum opening and lip margin of an eye to hold the implant in place in the canaliculus.

44. The method of claim 43 wherein said step of urging includes using a tool to urge the implant through the punctum opening and into a canaliculus.

* * * * *